US00PP33796P2

(12) United States Plant Patent
Kleinwee

(10) Patent No.: US PP33,796 P2
(45) Date of Patent: Dec. 28, 2021

(54) ***PETUNIA* PLANT NAMED 'PEHY0066'**

(50) Latin Name: *Petunia hybrida*
Varietal Denomination: PEHY0066

(71) Applicant: SYNGENTA CROP PROTECTION AG, Basel (CH)

(72) Inventor: Theodorus Cornelis Maria Van Kleinwee, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/064,913

(22) Filed: Oct. 7, 2020

(51) Int. Cl.
*A01H 5/02* (2018.01)
*A01H 6/82* (2018.01)

(52) U.S. Cl.
USPC ..... Plt./356.1

(58) Field of Classification Search
USPC ..... Plt./356.1
See application file for complete search history.

*Primary Examiner* — Susan McCormick Ewoldt
(74) *Attorney, Agent, or Firm* — Dale Skalla

(57) ABSTRACT

A new *Petunia* plant named 'PEHY0066' particularly distinguished by its small sized, yellow to bronze colored flowers, medium early flowering and a semi-trailing plant habit.

1 Drawing Sheet

Latin name of the genus and species of the plant claimed: *Petunia hybrida.*

Varietal denomination: 'PEHY0066'.

BACKGROUND OF THE NEW PLANT

The present invention comprises a new *Petunia*, botanically known as *Petunia hybrida*, and hereinafter referred to by the variety name 'PEHY0066'.

'PEHY0066' is a product of a planned breeding program. The new cultivar has small sized, yellow to bronze colored flowers, medium early flowering and a semi-trailing plant habit.

'PEHY0066' originated from a hybridization made in October 2015 in a controlled breeding environment in Enkhuizen, The Netherlands. The female parent was the proprietary selection 'N3118-1V', having a bigger flower shape, a light yellow flower color with deep yellow throat and a similar plant vigor but a more mounding plant habit compared to 'PEHY0066'.

The male parent of 'PEHY0066' was the proprietary selection 'P0266V', having a similar flower size, a deep yellow flower color, and a more trailing and more vigorous plant habit compared to 'PEHY0066'.

The resulting seeds were sown in January 2016. 'PEHY0066' was selected as one flowering plant within the progeny of the stated cross in May 2016 in a controlled environment in Enkhuizen, The Netherlands.

The first act of asexual reproduction of 'PEHY0066' was accomplished when vegetative cuttings were propagated from the initial selection in June 2016 in a controlled environment in Enkhuizen, The Netherlands.

BRIEF SUMMARY OF INVENTION

Horticultural examination of plants grown from cuttings of the plant initiated in June 2015 and continuing thereafter, has demonstrated that the combination of characteristics as herein disclosed for 'PEHY0066' are firmly fixed and are retained through successive generations of asexual reproduction.

'PEHY0066' has not been observed under all possible environmental conditions. The phenotype may vary significantly with variations in environment such as temperature, light intensity, and day length.

A Plant Breeder's Right for this cultivar has not yet been applied for. 'PEHY0066' has not been made publicly available prior to the effective filing date of this application, notwithstanding any disclosure that may have been made less than one year prior to the effective filing date of this application by the inventor or another who obtained 'PEHY0066' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawings show typical flower and foliage characteristics of 'PEHY0066' with colors being as true as possible with an illustration of this type.

Figure 1:
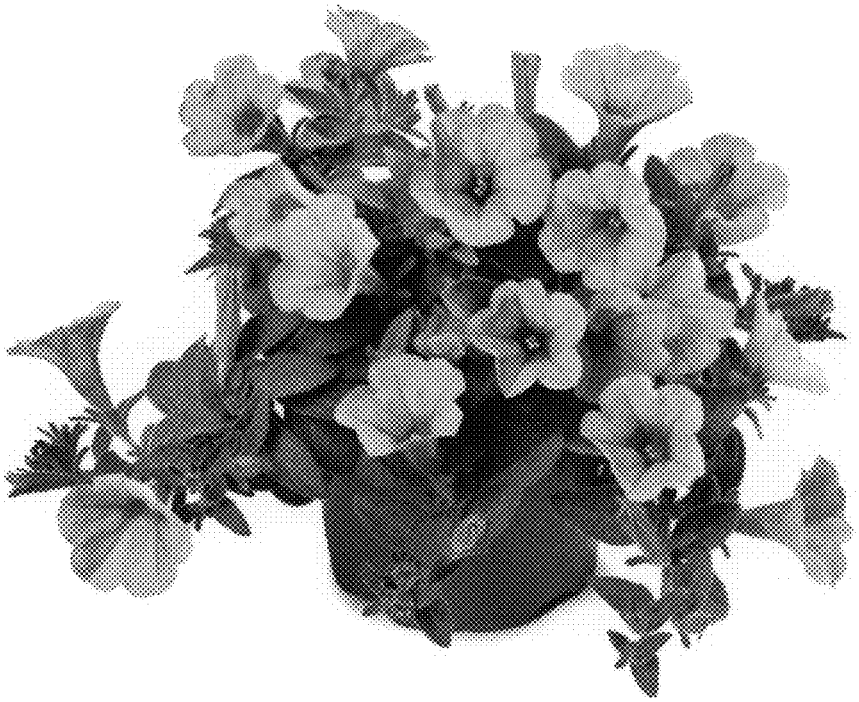
Figure 2:
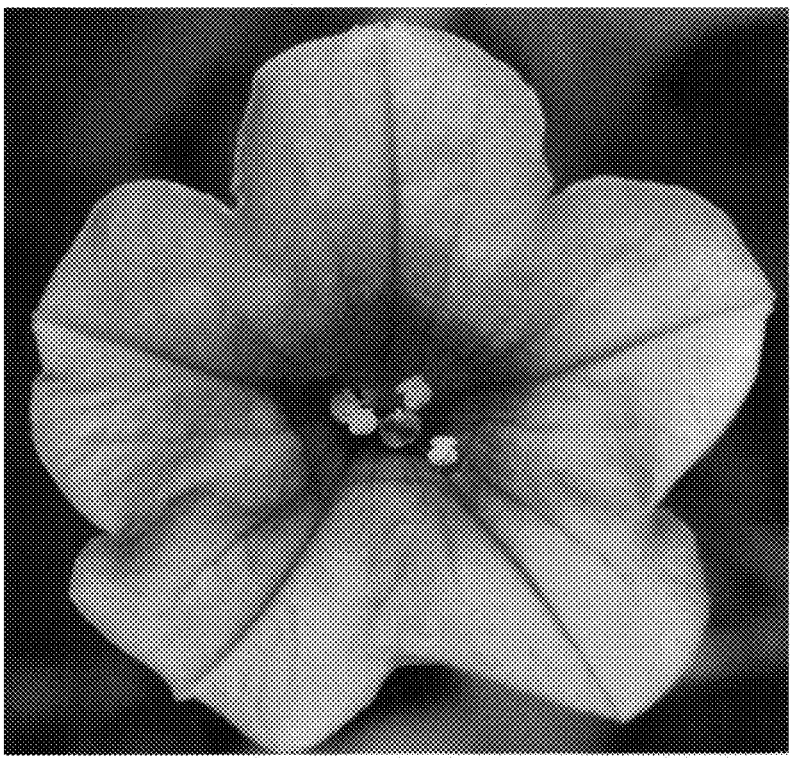

The photographic drawings show in FIG. 1. a flowering plant of the new variety and in FIG. 2. a close-up of the flowers.

DETAILED BOTANICAL DESCRIPTION

The aforementioned photographs were taken in April 2019 from plants growing indoor in 12 cm pots in Andijk, The Netherlands. These plants were approximately 11 weeks of age.

The plant descriptions and measurements were taken in September 2020 in Andijk, The Netherlands on approximately 21 week old plants that were growing in containers.

Color references are made to The Royal Horticultural Society Colour Chart (R.H.S.) 2001.

TABLE 1

DIFFERENCES BETWEEN THE NEW VARIETY 'PEHY0066' AND A SIMILAR VARIETY

| | 'PEHY0066' | 'Indian Summer (Not patented) |
|---|---|---|
| Plant habit: | Semi-trailing | Trailing |
| Flower color: | Yellow, bronze veins | Varying from yellow to bronze |
| Flower size: | Small | Medium |

Plant:
- *Form, growth and habit.*—Semi-trailing plant habit.
- *Plant height.*—18 cm.
- *Plant height (inflorescence included).*—22 cm.
- *Plant diameter (width).*—Approximately 30 cm.

Roots:
- *Number of days to initiate and produce roots.*—16 days at about 22° C.
- *Type.*—Fine, fibrous, free branching.
- *Color.*—RHS N158D.

Foliage:
- *Arrangement.*—Alternate, simple; sometimes opposite, decussate.
- *Immature leaf, color upper surface.*—RHS 143A.
- *Immature leaf, color lower surface.*—RHS 146B.
- *Mature leaf, color upper surface.*—RHS 146A.
- *Mature leaf, color lower surface.*—RHS 146B.
- *Length.*—2.8 cm.
- *Width.*—1.1 cm.
- *Shape.*—Elliptic.
- *Base shape.*—Shortly attenuate.
- *Apex shape.*—Acute.
- *Margin.*—Entire.
- *Texture, upper surface.*—Densely covered with short hair.
- *Lower surface.*—Densely covered with short hairs.
- *Color of veins, upper surface.*—RHS 144A.
- *Color of veins, lower surface.*—RHS 144A.
- *Petiole color.*—RHS 144A.
- *Length.*—0.2 cm.
- *Diameter.*—0.2 cm.
- *Petiole texture.*—Densely covered with short hairs.

Stem:
- *Quantity of main branches per plant.*—4-5.
- *Color of stem.*—RHS 144A.
- *Length of stem.*—18 cm.
- *Diameter.*—0.3 cm.
- *Length of internodes.*—1.4-2.5 cm.
- *Texture.*—Dense, mostly glandular short hairs.
- *Color of pedicel.*—RHS 146C.
- *Length of pedicel.*—2.0 cm.
- *Diameter of pedicel.*—0.2 cm.
- *Texture of pedicel.*—Densely covered with short hairs.

Inflorescence:
- *Type.*—Flowers solitary in upper leaf axis.
- *Floret type.*—Funnel-shaped; 5 lobed petals; fused at base.
- *Blooming habit.*—Medium early flowering in greenhouse, flowering throughout the summer months.
- *Quantity of inflorescences per plant.*—Approximately 90.
- *Lastingness of individual blooms on the plant.*—About 7 days.
- *Fragrance.*—Rather strong smell.

Bud (just when opening):
- *Color.*—RHS N144B at top, RHS N144D towards base.
- *Length.*—3.0 cm.
- *Width.*—1.0 cm.
- *Shape.*—Oblong.

Immature inflorescence:
- *Flower horizontal diameter.*—2.5 cm.
- *Color petals, upper surface.*—RHS 1A.
- *Color petals, lower surface.*—RHS 1B.

Mature flower:
- *Flower horizontal diameter.*—3.4 cm.
- *Flower height (vertical).*—2.0 cm.
- *Color upper surface.*—RHS 1A, veins RHS N34C.
- *Color lower surface.*—RHS 1B.
- *Conspicuousness of veins (conspicuousness is determined by color contrast and the number of contrasting veins).*—Medium.
- *Apex shape.*—Rounded.
- *Margin.*—Entire.
- *Waviness of margin.*—Low.
- *Petal lobing.*—Medium (not absent, not weak, not strong).
- *Petal texture, upper surface.*—Smooth.
- *Petal texture, lower surface.*—Smooth, occasionally a short hair.
- *Corolla tube color outside.*—RHS 1B.
- *Corolla tube color inside.*—RHS N34C, base RHS 146C.
- *Corolla tube: conspicuousness of veins on inner side (conspicuousness is determined by the color contrast and the number of contrasting veins).*—Medium.
- *Corolla tube length.*—1.5 cm.
- *Corolla tube texture, outside.*—Rather dense and short glandular hairs.
- *Corolla tube texture, inside.*—Glabrous.

Calyx:
- *Color of sepal, upper surface.*—RHS 146A, RHS 146B towards base.
- *Color of sepal, lower surface.*—RHS 146B.
- *Length.*—1.1 cm.
- *Width.*—0.2 cm.
- *Shape.*—Ensiform.
- *Apex shape.*—Acute.
- *Base.*—Fused.
- *Margins.*—Entire.
- *Texture, upper surface.*—Rather densely covered with short glandular hairs.
- *Lower surface.*—Densely covered with short glandular hairs.

Reproductive organs:
- *Pistil.*—1.
- *Length.*—1.4 cm.
- *Style color.*—RHS 145C.
- *Style length.*—1.7 cm.
- *Stigma color.*—RHS 143A.
- *Stamens.*—
- *Quantity per flower.*—5.
- *Color of filaments.*—RHS 145D.
- *Length filaments.*—1.6 cm.
- *Anther color.*—RHS 60D.
- *Anther length.*—0.2 cm.
- *Anther shape.*—Elliptical.
- *Color of pollen.*—RHS 159D.

*Pollen amount*.—Medium; Pollen is not visible with bare eye.

*Fertility/seed set*.—Has not been observed on this hybrid.

*Disease/pest resistance*.—Has not been observed on this hybrid.

What is claimed is:

1. A new and distinct variety of *Petunia* plant named 'PEHY0066' substantially as illustrated and described herein.

* * * * *